United States Patent [19]

Whitney et al.

[11] 4,165,330

[45] Aug. 21, 1979

[54] ASYMMETRIC SYNTHESIS VIA OPTICALLY ACTIVE CHELATING AGENTS

[75] Inventors: Thomas A. Whitney, Roselle; Arthur W. Langer, Jr., Watchung, both of N.J.

[73] Assignee: Exxon Research & Engineering Co., Florham Park, N.J.

[21] Appl. No.: 877,353

[22] Filed: Feb. 13, 1978

Related U.S. Application Data

[60] Continuation of Ser. No. 462,328, Apr. 19, 1974, abandoned, which is a division of Ser. No. 276,784, Jul. 31, 1972, abandoned.

[51] Int. Cl.$^2$ .................. C07F 7/08; C07C 29/14; C07C 31/18; C07C 33/00
[52] U.S. Cl. .................. 260/448.2 B; 260/563 C; 568/715; 568/808; 568/811; 568/813; 568/814; 568/852; 568/855; 568/862; 568/874; 568/878; 568/880
[58] Field of Search .............. 568/807, 715, 808, 811, 568/813, 814, 852, 855, 862, 874, 878, 880; 260/448.2 B

[56] References Cited

U.S. PATENT DOCUMENTS

| 3,200,106 | 8/1965 | Dickson | 260/448 B |
| 3,734,963 | 5/1973 | Langer et al. | 260/448 B |
| 3,758,585 | 9/1973 | Bunting | 260/583 P |
| 3,883,580 | 5/1975 | Solodar | 568/814 |

OTHER PUBLICATIONS

Nozaki et al., "Tetrahydron Letters", No. 38, pp. 4097–4098, 1968.
Dilts et al., "Inorg. Chem.", vol. 9 (1970), No. 4, pp. 855–862.
Msurits, Diss. Abstract Int. B, vol. 30 (11) (1970), p. 4950.
Winternitz et al., "Chem. Abstracts", vol. 50 (1956), columns 14573–14575.

Primary Examiner—Joseph E. Evans
Attorney, Agent, or Firm—J. P. Corcoran; J. J. Allocca

[57] ABSTRACT

An asymmetric synthesis process which involves addition of optically active chelated organometal compounds of lithium, sodium, beryllium, magnesium, zinc, copper and cadmium to prochiral unsaturated substrates. The optically active chelating agent is not consumed and can be recycled.

6 Claims, No Drawings

ASYMMETRIC SYNTHESIS VIA OPTICALLY ACTIVE CHELATING AGENTS

CROSS REFERENCE TO RELATED CASES

This is a continuation of application Ser. No. 462,328, filed Apr. 19, 1974, now abandoned, which in turn is a division of application Ser. No. 276,784 filed July 31, 1972, now abandoned.

This invention relates to an asymmetric synthesis process. In one aspect, this invention relates to an asymmetric synthesis process which reacts optically active chelated organometal compounds with prochiral unsaturated substrates. In another aspect, this invention relates to the formation of a class of optically active chelate compositions.

One of the coinventors of the subject application, has disclosed and claimed in U.S. Pat. No. 3,451,988 various compositions of matter which are prepared by mixing organometallic compounds with selected bifunctional Lewis bases. However, these compounds are not optically active.

H. Nozaki, T. Aratani and T. Toraya, *Tetrahedron Letters*, 4097 (1968) disclose the reaction of sparteine•n-butyl lithium with benzaldehyde to afford an optically active carbinol. Sparteine is a natural product occurring in a plant called "broom tops" and is available in only one absolute configuration.

The problem with having only one absolute configuration of the chiral chelating agent is that it allows the synthesis of only one optical isomer of a product which may not be the desired enantiomer or epimer. In the synthesis of compounds having biological activity or medicinal value, it is essential that one be able to prepare all desired enantiomers or epimers. For this reason, synthetic optically active chelating agents are preferred and in many cases are essential for effecting stereoselective synthesis of the desired stereoisomer. (For example, naturally occurring sparteine complexed with n-butyllithium reacts with benzaldehyde to yield (+)-1-phenyl-1-pentanol. The (−)-isomer cannot be prepared via this route using naturally occurring sparteine). Therefore, the availability of both optical isomers of synthetic chelating agents permits the synthesis of either or both optical antipodes of a product in which a new asymmetric center is created. In addition, the synthetic optically active chelating agent can be tailor-made to provide maximum stereospecificity.

The optically active chelates of this invention have the formula: Chel*•M-$Z_m$ and Chel*•M$Z_m Y_n$ wherein Chel* has a formula selected from the group:

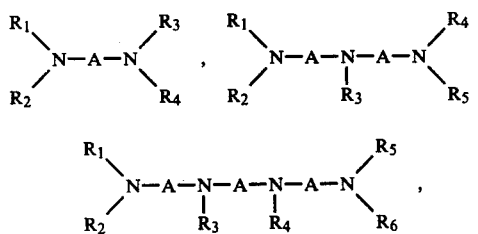

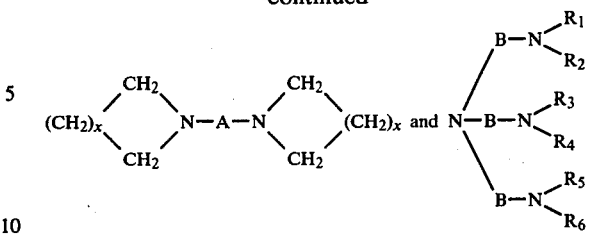

wherein $R_1$ is a $C_1$ to $C_{20}$ hydrocarbyl radical; $R_2$, $R_3$, $R_4$, $R_5$ and $R_6$ are the same or different alkyl or aryl radicals of 1 to 7 carbon atoms inclusive; A is selected from the group consisting of a nonreactive group containing 2 to 3 methylenic radicals having 1 to 6 monovalent substituents containing 1 to 10 carbon atoms, or a cycloaliphatic radical and their lower alkyl or naphthenic derivatives having ring structures containing 5 to 7 members wherein said radicals are attached to the nitrogen atoms at adjacent positions on the rings and B is selected from the group consisting of a nonreactive group containing 2 to 3 methylenic radicals having 1 to 3 monovalent substituents containing 1 to 10 carbon atoms such that the chelating polytertiary amine does not have a center, plane or alternating axis of symmetry; x is an integer of 0 to 3 inclusive; M is a metal selected from the group consisting of lithium, sodium, beryllium, magnesium, zinc, copper and cadmium; Z is a reactive anion selected from the group consisting of $C_1$-$C_{30}$ alkyl, $C_6$-$C_{30}$ aryl, $C_7$-$C_{30}$ aralkyl, $C_3$-$C_{30}$ naphthenic, $C_2$-$C_{30}$ alkenyl, $C_2$-$C_{30}$ alkynyl, $AlH_4$, $BH_4$, $AlH_3OR_1$, $AlH_2(OR_1)_2$, $AlH(OR_1)_3$, $BH_3OR_1$, $BH_2(OR_1)_2$, $BH(OR_1)_3$, $AlH_3N(R_1)_2$, $AlH_2[N(R_1)_2]_2$, $AlH[N(R_1)_2]_3$, $AlH_3Cl$, $R_1R_1'C^{\ominus}CO_2$,

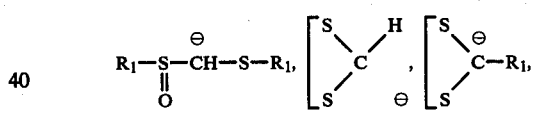

$R_1HC^{\ominus}CO_2$, $R_1R_1'C^{\ominus}CO_2R_1$, $R_1R_1'C^{\ominus}CO_2R_1$, m is 1 or 2 depending on the valence of M; n is 0 or 1; and Y is an inert anion such as halide, alkoxide, secondary amides, and mercaptides; * denotes optical activity.

Suitable nonlimiting examples of M—$Z_m$ include $LiC_4H_9$, $NaC_6H_5$, $LiCu(C_4H_9)_2$, $Mg(C_4H_9)_2$, $Zn(C_2H_5)_2$, $LiC_6H_4C_{24}H_{49}$, $Be(C_4H_9)_2$, $Cd(CH_3)_2$, $LiCH_2$—$CH$=$CH$—$C_6H_{13}$, $LiC$≡$C_{19}H_{39}$, $LiCH(CH_3)[CH(CH_3)]_2CH(C_6H_{11})C(CH_3)_3$, $(CH_3)_3CCH$=$CHNa$, $LiCH_2C_6H_5$, $NaC_{10}H_7$, $Cd(C_7H_{15})_2$, $LiC_{30}H_{61}$, $NaC(C_6H_5)_3$, $LiCH(C_6H_5)_2$, $Cd(C_6H_5)_2$, $LiCH_2CH_2CH_2CH(C_5H_9)_2$, $NaCH(C_6H_5)_2$, $LiAlH_4$, $NaAlH_4$, $LiAlH_3OCH_3$, $NaAlH_3OC_6H_{13}$, $LiAlH_2(OC_6H_5)_2$, $NaAlH_2(OC_{12}H_{25})_2$, $LiAlH(OC_4H_9)_3$, $NaBH(OC_2H_5)_3$, $LiAlH_3N(CH_3)_2$, $LiAlH_2[N(C_3H_7)_2]_2$, $NaAlH[N(C_6H_{11})_2]_3$, $LiAlH_2Cl_2$, $NaAlHBr_3$.

In addition, compounds MZ may be derived by metalation or organic substrates having at least one metalatable hydrogen atom whose pKa is between 15 and 39 on the MSAD scale, ("Fundamentals of Carbanion Chemistry", D. J. Cram, Academic Press, New York, 1965, p. 19), by using LiZ and NaZ compounds in which the pKa of HZ is higher than that of the organic substrate to be metalated. Suitable nonlimiting examples of such substrates include $CH_3SCH_2SCH_3$,

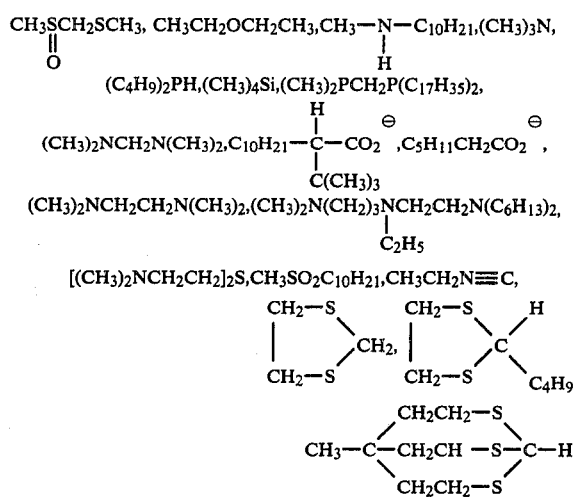

pyrrole, cyclopentadiene, etc.

Suitable examples of compounds having the formula $MZ_mY_n$ include $CH_3MgCl$, $C_6H_5MgOCH_3$, $(CH_3)_2CHBeSC_2H_5$, $CH_3ZnSCH_3$, $C_{10}H_{21}CdOC_{10}H_{21}$, $C_6H_{11}MgBr$, $C_3H_7MgN(CH_3)_2$, $C_4H_9MgI$, $C_4H_9MgBr$, $C_5H_{11}CdBr$, $C_6H_{13}BeOC_6H_5$, $C_6H_5CuI$, $C_6H_5CuOC_2H_5$, $CH_3MgSCH_3$, $CH_3ZnSC_{12}H_{25}$, $C_6H_5MgOC_6H_{11}$,

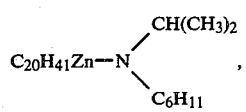

$CH_2=CHCH_2MgI$.

Preferred optically active chelating agents are those having the above formulas in which $R_1$ is a $C_1$ to $C_{20}$ hydrocarbyl radical; $R_2$, $R_3$, $R_4$, $R_5$ and $R_6$ are the same or different alkyl radicals of 1 to 4 carbon atoms inclusive; A is selected from the group consisting of a nonreactive group containing 2 to 3 methylenic radicals having 1 to 3 monovalent substituents containing 1 to 10 carbon atoms or a cyclohexyl radical and its lower alkyl or naphthenic derivatives wherein said radical is attached to the nitrogen atoms in a trans fashion at adjacent positions on the ring such that the chelating polytertiary amine does not have a center, plane or alternating axis of symmetry, and x is 2 or 3.

Particularly preferred optically active chelating agents of this invention are those diamines and triamines having the above formulas in which $R_1$ is a $C_1$ to $C_{20}$ hydrocarbyl radical; $R_2$, $R_3$, $R_4$ and $R_5$ are methyl groups; A is selected from the group consisting of a nonreactive group containing 2 methylenic radicals having 1 to 2 monovalent substituents containing 1 to 10 carbon atoms or a cyclohexyl radical and its lower alkyl or naphthenic derivatives having a ring structure containing 6 members, wherein said radical is attached to the nitrogen atoms in a trans fashion, at adjacent positions on the ring such that the chelating polytertiary amine does not have a center, plane or alternating axis of symmetry, and x is two.

Furthermore, in all of the above formulas, one or more R groups may be optically active radicals. In such cases, it is not essential that Group A also be chiral and optically active. Thus, chelating agents having the structures:

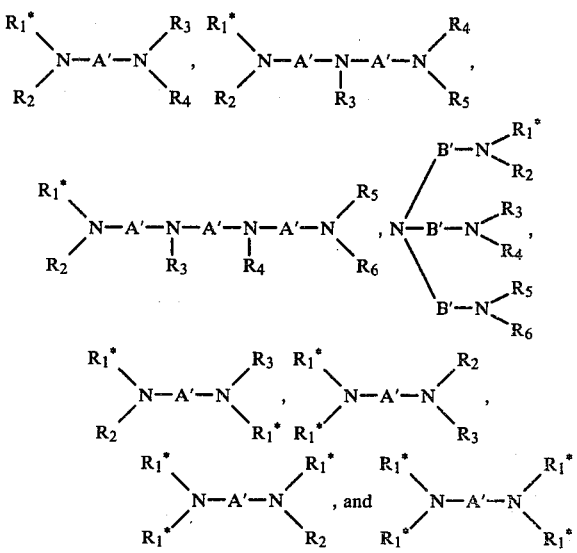

are claimed as part of this invention wherein $R_1^*$ is a $C_4$ to $C_{20}$ hydrocarbyl group containing at least one resolved asymmetric carbon atom which is removed no more than 4 carbon atoms from the nitrogen atom; A' is a nonreactive group containing 2 to 3 methylenic radicals or a cycloaliphatic radical and their lower alkyl or naphthenic derivatives having ring structures containing 5 to 7 members wherein said radicals are attached to the nitrogen atoms at adjacent positions on the rings; B' is a nonreactive group containing 2 to 3 methylene radicals; $R_2$–$R_6$, M, Z, m, n and Y are as defined previously. Obviously, the chelating agent may contain more than one optically active R group as long as the resultant tertiary amine chelating agent does not contain a center, plane or alternating axis of symmetry. In the preferred structures, the non-optically active R groups are methyl groups.

Suitable nonlimiting examples of optically active chelating agents claimed in this invention include compounds having the following structures:

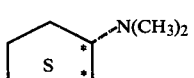

TMCHD

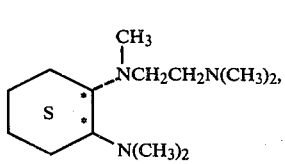

PM-1,2-CHD

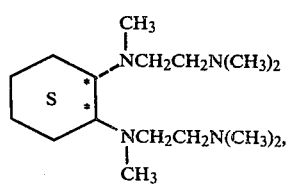

-continued
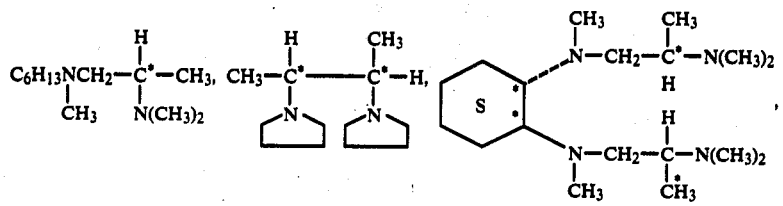
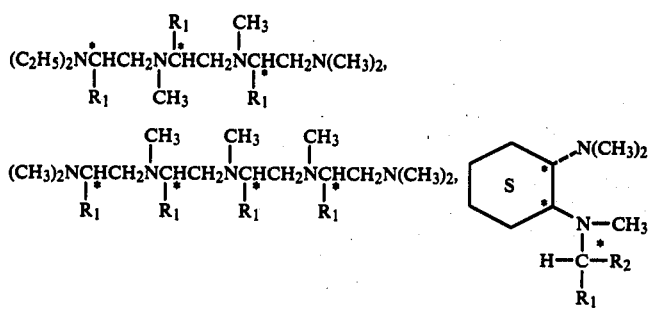
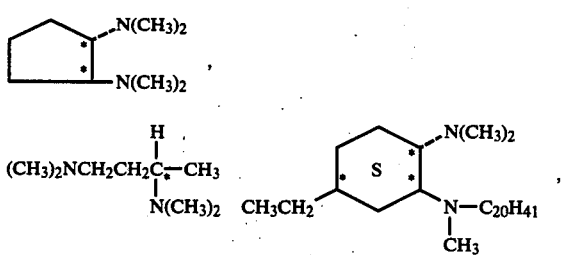
TM-1,3-BD
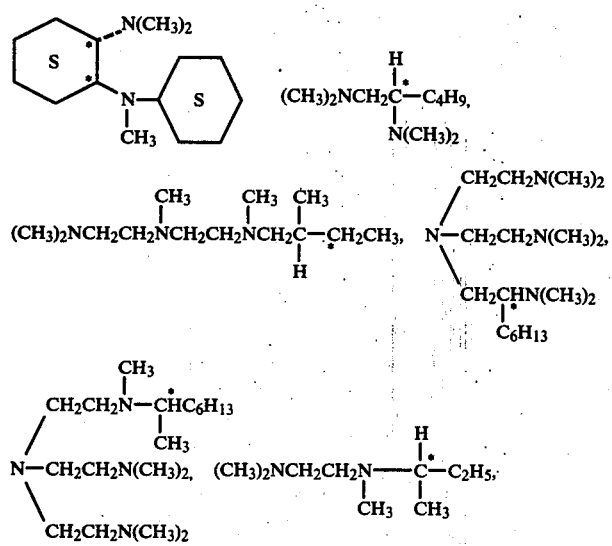
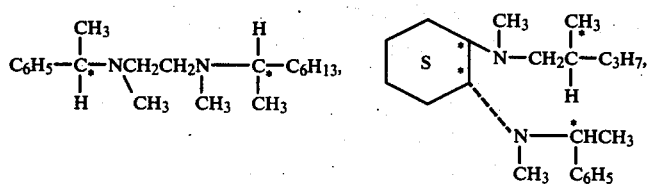
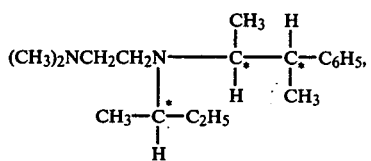

-continued

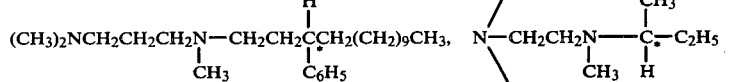
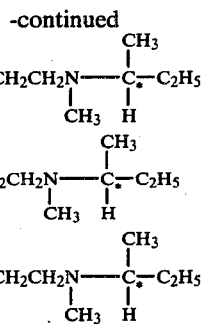

The optically active chelates derived from 1,2 cyclohexane-diamine (DACH) as defined hereinabove are prepared from optically active DACH which is obtained by the optical resolution of racemic trans-DACH via its neutral d-tartrate salt to initially afford (—)DACH. This optical resolution is known in the prior art [R. G. Asperger and C. F. Liu, "Inorganic Chemistry" 4, page 1492 (1965)], (—)DACH may then be methylated via the Eschweiler-Clarke procedure (H. T. Clarke, H. B. Gillespie and S. Z. Weisshaus, "J. Am. Chem. Soc.", 55, 4571 (1933) to prepare (—) N,N,N',N'-tetramethylcyclohexanediamine ((—)-TMCHD).

From the mother liquors remaining after the separation of the neutral d-tartrate of (—)DACH, it is known in the art (F. M. Jager and L. Bijkerk, "Proc. Akad. Sci. of Amsterdam" 40, P12 (1937)) that the acid d-tartrate of (+)DACH may be precipitated by adding an additional equivalent of d-tartaric acid and ethanol. The acid d-tartrate of (+)DACH of low optical purity is then converted to (+)DACH·2HCl and the latter is fractionally crystallized from water to obtain (+)DACH·2HCl of greater optical purity. This process is very inefficient and optical yields are quite low.

It has been found that (+)DACH of high optical purity and high chemical purity may be obtained from low optical purity and low chemical purity DACH recovered from the basicified mother liquors left after separation of (—)DACH d-tartrate by carefully controlled fractional crystallization of said impure (+)DACH either neat or from hydrocarbon solution.

Furthermore, it has been found that (+)TMCHD of very high chemical purity and high optical purity may be prepared from said impure (+)DACH by methylation (loc.cit.) of the whole followed by fractional crystallization of a (+)TMCHD inorganic lithium salt chelate from hydrocarbon medium. This process is far more efficient and affords improved optical and chemical yields of (+)TMCHD over the method of securing (+)DACH via its acid d-tartrate followed by dihydrochloride fractional crystallization and subsequent methylation.

The optically active chelates as defined hereinabove which are not derived from DACH are prepared from other suitable optically active polyamines. For example, it is known in the prior art [Francis P. Dwyer, Francis L. Garvan and Albert Shulman, "J. Am. Chem. Soc." 81, 290 (1959)] that racemic 1,2-propanediamine may be resolved into its optical antipodes using d-tartaric acid as the resolving agent. Both the (+) and (—)-isomers may be obtained which could then be methylated via the Eschweiler-Clarke reaction to afford TM-1, 2-PD (N,N,N',N'-tetramethyl-1,2-propanediamine).

Higher homologs, i.e., triamines could be also prepared using optically active 1,2-propanediamine as starting material. Thus, reaction of the diamine with one equivalent of n-butyllithium to give the mono-lithioamide followed by reaction of the latter with $(CH_3)_2NCH_2CH_2Cl·HCl$ would give

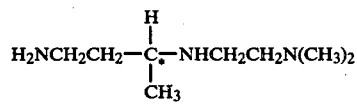

and

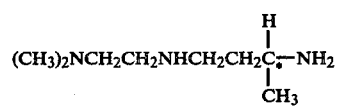

which could then be methylated via the Eschweiler-Clarke reaction.

Alternatively, optically active 1,2-propanediamine or its conjugated base could be reacted with an optically active organic compound containing a displaceable group, such as halide or tosylate, to yield a product having an additional asymmetric center attached to nitrogen. An example of such a reaction is shown below:

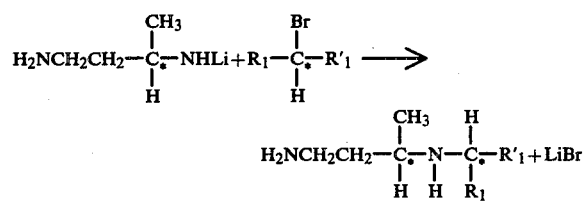

This process could be repeated to introduce additional asymmetric centers into a chelating polyamine. Finally, the Eschweiler-Clarke reaction would afford the N-peralkylated optically active chelating polyamines of the subject invention. Extensions and variations of the above schemes are apparent to one skilled in the art.

The molar ratio of the chelating agent to the M—$Z_m$ may be in the range of about 10:1 to 1:10, preferably 2:1 to 1:2 and most preferably at 1:1.

An electrophilic reaction on unsaturated substrates can be depicted schematically by the reaction of an optically active chelate compound (Chel*·$MZ_m$ or Chel*·$MZ_mY_n$) with a prochiral unsaturated compound.

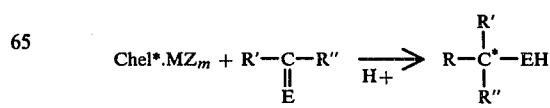

Z and m are as defined previously. The structures of R′ and R″ are not critical as long as they are different from each other before and after reaction with the optically active chelate compounds. R will equal Z except when Z is a borohydride or aluminum hydride group or a derivative thereof, such as $AlH_3Cl$ or $BH_2(OR)_2$, in which case R is hydrogen obtained from the hydride. R′ and R″ are groups such as hydrogen, alkyl, aryl, aralkyl, alkaryl, naphthenic, etc., and may contain one or more functional groups such as olefin, acetylene, ether, thioether, primary, secondary or tertiary amine, imine, amide, ketal, acetal, hydroxyl, thiol, nitrile, sulfoxide, sulfone, nitro, ester, carboxyl, halide, phosphine, silane, germane, stannane and metallocene. It is understood that $M-Z_m$ may react with some functional groups in R′ and R″ as long as the reaction does not produce two identical groups attached to the asymmetric atom or prevent reaction at the prochiral center when excess $M-Z_m$ is present. Each R′ and R″ group will normally contain less than about 30 carbon atoms and may be connected such as to form ring structures as long as the substrate is a prochiral compound. E equals O, S or a monosubstituted nitrogen radical. Thus, the unsaturated prochiral functional groups are carbonyl, thiocarbonyl or unsaturated imino. Suitable unsaturated prochiral substrates include compounds having functional groups such as aldehydes, ketones, $\alpha,\beta$-unsaturated carbonyl compounds such as $RCH=CH-CO_2R'$ or $RCH=CH-CONR'_2$, thioaldehydes, thioketones, imines, oximes, hydrazones, semicarbazides, osazones, and related compounds. Preferred functional groups in the prochiral substrate are selected from the group consisting of aldehydes, ketones, imines, oximes and hydrazones. Since R′ and R″ groups are not critical, some representative, non-limiting examples are listed for illustrative purposes: benzaldehyde, acetophenone, benzil mono-oxime, butyraldehyde, 2-octanone, octadecyl naphthyl ketone, ethyl cyclohexyl ketone, methyl crotonate, furaldehyde, phenylsulfonylacetone, $\beta$-acetylpyridine, thiobenzaldehyde, phenylcyclohexyl thioketone, N-phenylbenzaldimine, phenylacetaldimine, methyl 2-butyl ketoneoxime, ethylpyruvate phenyl hydrazone, glucose phenylosazone, 3-hydroxypropyl methyl ketone, 2-ethoxyethyl methyl ketone, o-dimethylaminobenzaldehyde, 1-ferrocenyl-4-pentanone, $CH_3SO_2CH_2CH_2COCH_3$, $(CH_3)_2PCH_2CH_2CH_2CH_2CH(CH_3)COC_2H_5$, $ClCH_2CH_2CH_2COCH_3$, $(CH_3)_3SiCH_2CH_2COCH_3$, $(CH_3)_3SiCOC_6H_5$, $(CH_3)_3GeCH_2CH_2COCH_3$, $(CH_3)_3SnCH_2CH_2COCH_3$, $C_6H_5COCO_2H$, $CH_3SCH_2CH_2COC_6H_5$, $CH_2=CHCH_2CH_2CH_2COC_6H_{11}$, $CH_3C\equiv CCH_2CH_2COCH(CH_3)_2$

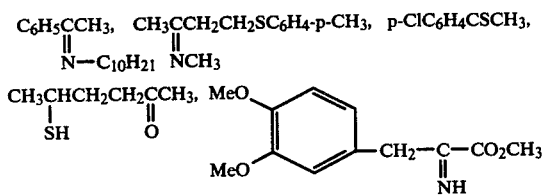

Any inert solvent may be used for reaction of the optically reactive chelates with unsaturated prochiral substrates.

This reaction can be carried out in the presence of any solvent which is inert to Chel*•$MZ_m$ or Chel*•$MZ_mY_n$. For example, aromatic hydrocarbons may be used except in those cases where the complex is reactive enough to metalate aromatic compounds. In those cases, saturated hydrocarbon solvents are preferred. The reaction can be run at any convenient temperature, i.e. from $-100°$ to $+100°$ C. but generally lower temperatures, ranging from $-80°$ to $30°$ C. are preferred.

The mole ratio of the optically active chelate to the prochiral substrate may be in the range of 10:1 to 1:10, preferably 2:1 to 1:2 and most preferably about 1:1 based on the number of reactive groups in the optically active chelate and in the prochiral substrate.

Other optically active chelates that may be employed is asymmetric syntheses of this invention include those in which the anion has the formula

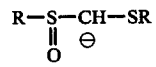

and $(RS)_3C^\ominus$. Products containing these radicals may be converted to aldehydes and acids. Hence a synthesis of optically active $\alpha$-amino acids can be formulated:

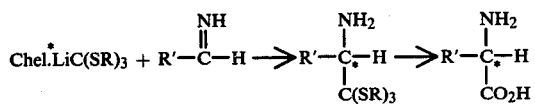

By means of this invention, well known compounds having medicinal value or other important biological properties may be prepared in optically active forms by choice of the proper prochiral substrate. Such compounds include d-desoxyephedrine, l-ephedrine, L-DOPA, l-epinephrine, l-methanol, mephenesin [3-(o-tolyloxy)-1,2-propanediol], certain sugar stereoisomers, alanine, phenylalanine and tyrosine, etc.

Another aspect of this invention relates to the use of the optically active chelated complex metal hydrides for preparation of optically active sulfoxides and phosphine oxides and phosphines via partial reduction of such chiral compounds. This aspect of the invention is illustrated by the following equations:

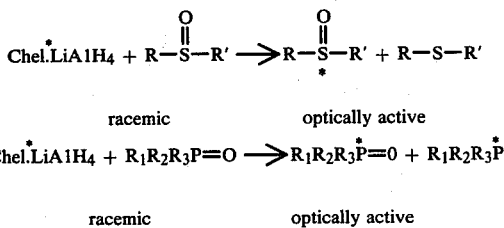

In practicing this aspect of the present invention, the mole ratio of Chel*•$LiAlH_4$ to racemic sulfoxide or phosphine oxide is chosen so as to avoid complete reduction. Generally, the reduction is carried to from about 10% to 90% of completion, preferably to about 50% of completion and the recovered unreduced phosphine oxide or sulfoxide is found to be optically active.

Still another aspect of this invention is the use of optically active organolithium chelates, Chel*•$LiR_7$, to metalate polymers and then to react the optically active chelated metalated polymer species with a prochiral substrate thereby yielding polymers with optically active functional groups. The general polymer metalation process is the subject of copending application Ser. No.

690,076 filed Dec. 13, 1967 now U.S. Pat. No. 4,060,700. This aspect of the invention is illustrated as follows for polystyrene:

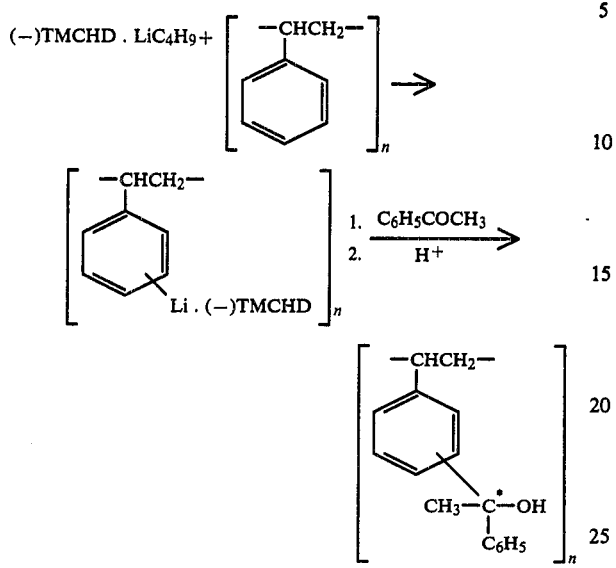

The mole ratio of the optically active metalating agent to the polymer monomer unit may vary widely depending upon the degree of functionalization desired, but will normally be about 1:1000 to 1:1. $R_7$ is selected from the group consisting of $C_1$ to $C_{20}$ alkyl, aryl, aralkyl, naphthenyl or alkaryl radicals.

This invention is illustrated by the following examples.

EXAMPLE 1: Preparation of Optically Active (+)- and
(−)-N,N,N'N'-Tetramethyl-1,2-cyclohexanediamine
((+)-and (−)-TMCHD)

To 2 liters of water was added 333.3 g (2.92 moles) of impure 1,2-diaminocyclohexane (DACH) and the solution was warmed to about 60° C. To the warm solution was added 440 g (2.92 moles) of d-tartaric acid in small portions. An additional 920 ml of water was added as the d-tartaric acid was being added. The temperature of the final reaction mixture was 90° C. To the hot homogeneous solution was added a few seed crystals of (−)-DACH tartrate and the whole was allowed to slowly cool to room temperature, stand at room temperature for 2 days and was then cooled to 0°–5° C. for 2 more days.

Two additional batches were prepared exactly as described above. All three batches of DACH tartrate were then filtered and the residue was dried, wt. 542 gm (crop 1) total.

The mother liquor from the filtration was concentrated in a rotary evaporator until the total volume was about 4.5 liters and additional tartrate salt desposited which was recovered by filtration, wt. 267 g (Crop 2). An additional crop of tartrate salt separated upon further concentration of the mother liquor to about 2 liters, wt. 180 g (Crop 3).

Crop 1 DACH tartrate, wt. 541.5 g, and one liter of water were placed in a two liter continuous extraction apparatus. Enough 50% NaOH solution was added to make the mixture strongly basic and the mixture was extracted with benzene until no more DACH was found in the extract. The benzene was removed from the crude optically active DACH and the latter was distilled, b.p. 71–73/8 mm, wt. 216 g $[\alpha]_{589}^{25} = -40.3°$ (C=5.23, benzene) which corresponds to 97% optical purity. This value was determined by converting (−)-DACH·2HCl of $[\alpha]_{589}^{23} = -15.6°$ (C, 0.2 g per ml H$_2$O), (lit. R. G. Asperger and C. F. Liu, "Inorganic Chemistry", 4 1493 (1965), $[\alpha]_{589} = -15.8°$ (C, 0.2 g per ml H$_2$O)), to the free amine and then determining that optically pure (−)DACH has a rotation of $[\alpha]_{589}^{25} = -41.4°$ (C=5, benzene). (−)DACH was found to be rather insensitive in its specific rotation to concentration changes in benzene over the range C=5.871 to C=4.00 grams per 100 ml: $[\alpha]_{589}^{25} = -41.0°$ (C=5.871); $[\alpha]_{589}^{25} = -42.0°$ (C=4.00).

Cut-back of Crop 2 DACH tartrate in the same manner as Crop 1 gave 70 g of (−)DACH having $[\alpha]_{589}^{25} = -33.6°$ (C=4.92, benzene) which corresponds to 80.6% optical purity.

The mother liquor remaining after Crop 3 DACH tartrate separated was treated as described for the Crop 1 tartrate and 540 g of distilled product was obtained which displayed $[\alpha]_{589}^{25} = +20.3°$ which corresponds to 48.7% optical purity assuming that the product was chemically pure. (That the recovered (+)-DACH was not chemically pure, even though the GC of the material on a Carbowax 20M-KOH column showed only one peak, will be shown below).

Optically pure (+) or (−)-DACH has a melting point of 43°–44° C. while racemate is a liquid. Thus, trans-1,2-diaminocyclohexane is a racemic mixture and partially optically pure material may be made more nearly optically pure by careful fractional crystallization of the neat material from a melt. (For a discussion of the different types of behavior of chiral compounds see Stereochemistry of "Carbon Compounds" by Ernest L. Eliel, McGraw-Hill, Inc., New York 1962, Chapters 1 and 2).

The procedure of upgrading partially optically pure DACH via fractional crystallization from the melt or from hydrocarbon solution is a very facile means of obtaining (+)-DACH of high optical purity. This procedure is considerably superior to that of the literature (R. G. Asperger and C. F. Liu, "Inorganic Chemistry" 4 1492 (1965) which involves forming the bitartrate of (+)-DACH after separation of (−)-DACH tartrate, precipitation of the former by addition of ethanol to the hot bitartrate solution, converting the (+)-DACH bitartrate to the dihydrochloride, fractionally crystallizing the dihydrochloride from water and finally hand picking the optically active (+)-DACH dihydrochloride crystals from the featherlike aggregates of racemic salt.

The fractional crystallization technique was applied to 540 g of (+)-DACH having $[\alpha]_{589}^{25} + 20.3°$ (C 5.05 benzene). The material was placed in a Schlenk tube which was placed in a constant temperature bath at 20° C. Over a period of 19 days the temperature of the bath was slowly lowered to 9° C. as a crop of crystals grew. After this period of time the Schlenk tube was inverted and the solids were filtered from the mother liquor. The arm of the Schlenk tube containing the solids was heated and the molten (+)-DACH was removed from the tube with a pipette. It displayed $[\alpha]_{589}^{25} + 38.7°$ (C 5.32 benzene) which is 94% optically pure: 137.9 g was obtained. The mother liquor, $[\alpha]_{589}^{25} + 13.4°$ (C 5.03), 331 g was charged into a new Schlenk tube and put back into the bath at 9° C. Over a period of 18 days the bath temperature was lowered to −3° C. as a second crop of crystals formed which were recovered and melted. This material displayed $[\alpha]_{589}^{25} +36.2°$ (C 5.23 benzene) or 87.5% optical purity, wt. 56.2 g. The mother liquor displayed $[\alpha]_{589}^{25} +8.22°$ (C 5.09 benzene).

Further cooling of the mother liquor did not afford additional (+)-DACH crystals. This behavior was strange because a prior batch of (+)-DACH of only +4.7° continued to deposit crystals when cooled as low as −5° C. It was concluded that most probably the (+)-DACH of +8.22° was impure and that the impurities were preventing the excess (+)-antipode from separating.

Therefore, 111 g (0.97 mole) of the (+)-DACH of $[\alpha]_{589}^{25} +8.22°$ was methylated via the Eschweiler-Clarke procedure (H. T. Clarke, H. B. Gillespie and S. Z. Weisshaus, "J. Amer. Chem. Soc." 55, 4571 (1933)) using 545 ml of 90% formic acid and 354 ml of 40% aqueous formaldehyde. The resulting (+)-trans-N,N,N',N'-tetramethyl-1,2-cyclohexanediamine ((+)-TMCHD) was found to have $[\alpha]_{589}^{25} +3.97°$ (neat) or 19.8% optical purity and 70.7% chemical purity by VPC analysis, wt. 153.3 g bp 70°–73° C. @ 4 mm. (Optically pure TMCHD has $[\alpha]_{589}^{25} \pm 17.2°$ (neat) d=0.888 @ 25° C. $[\alpha]_{589}^{25} \pm 52.9°$ (C 5.51, 95% ethanol) and $[\alpha]_{589}^{25} \pm 20.0°$ (C 5.06 benzene.))

To 150 g (∼231 mmoles) of the impure (+)-TMCHD of $[\alpha]_{589}^{25} +3.97°$ (neat) was added 50 ml of benzene and 20 g (231 mmoles) of LiBr. Then an additional 50 ml of benzene was added and the clear homogeneous solution was allowed to stand at room temperature for 13 days and a crop of crystals separated which were recovered by filtration and washed with 25 ml of pentane, wt. 45.7 g. The (+)-TMCHD was recovered from the LiBr chelate by dissolving the latter in water, making the solution strongly basic with NaOH and extracting the mixture with hexane. The recovered (+)-TMCHD displayed $[\alpha]_{589}^{25} +15.45°$ (C 5.60 benzene) or 77.2% optically pure and was 99+% pure by VPC analysis. Thus via chelation with lithium salts chemically and optically impure TMCHD may be upgraded in both chemical and optical purity in a single step process.

EXAMPLE 2

Into a beaker was put 0.19 g (5 mmole) of LiAlH$_4$, 25 ml of toluene and 0.85 g (5 mmole) of (−)-TMCHD, $[\alpha]_{589}^{25} -17.2°$ (neat) or 100% optically pure, and the mixture was stirred one hour at room temperature. The turbid gray mixture was cooled to −80° C. and a solution of 1.20 g (10 mmoles) of acetophenone in 10 ml of toluene was added dropwise while the reaction mixture was maintained at −70° to −80° C. When addition of acetophenone was complete the reaction mixture was maintained at −70° to −80° C. for about 30 minutes and then allowed to warm to 0° C. Water, 5 ml, was added followed by 30 ml of 1 N HCl. The liquid phases were separated and the aqueous phase was extracted with 15 ml of pentane. The combined organic phase was then extracted with 15 ml of 1 N HCl, 15 ml of 10% NaHCO$_3$ solution, 15 ml of H$_2$O, dried over Na$_2$SO$_4$ and finally concentrated on a rotary evaporator. By VPC analysis the product was 92% 1-phenyl-1-ethanol and 7.4% toluene; no (−)-TMCHD was present. The optical activity of the product was measured using a Perkin Elmer Model 141 polarimeter: $[\alpha]_{589}^{25} +2.94°$ (C 13.14 benzene) which corresponds to 6.3% optical purity by direct comparison with an authentic sample of optically pure 1-phenyl-1-ethanol. The NMR and IR spectra were the same as the reference compound.

The above results demonstrate unequivocally that optically active chelated lithium compounds may be employed in electrophilic addition reactions to afford optically active products without sacrificing one asymmetric center to create a new one. This is true as the sign of rotation of the product was opposite to that of the starting (−)TMCHD•Li AlH$_4$, and the chelating agent was recovered unchanged and used over and over again.

EXAMPLE 3

Following the general procedure described in Example 2, a variety of reactions were run using (+)-TMCHD•LiR and (−)-TMCHD•LiR chelates for asymmetric syntheses. Particular care was taken to ensure that the optically active chelating agent was completely removed from the products. All rotations were taken at 25° C. and the value reported for product optical purity are based on literature values of $\alpha$ max or direct measurements on authentic samples. The results of these experiments are summarized in the Table.

TABLE I

| Chelate | Substrate | Solvent | Product | $[\alpha]_{589}^{25}$ | Optical Purity, % |
|---|---|---|---|---|---|
| (−)TMCHD . LiC$_4$H$_9$ | C$_6$H$_5$COH | Pentane | C$_6$H$_5$C(OH)(C$_4$H$_9$)H | −1.8° (C, 14.3, B$^a$) | 5.8 |
| (−)TMCHD . LiC$_6$H$_5$ | C$_4$H$_9$COH | Pentane | C$_6$H$_5$CC$_4$H$_9$(OH)H | +2.96° (C, 13.3, B$^a$) | 9.5 |
| (−)TMCHD . LiAlH$_4$ | C$_6$H$_{13}$COCH$_3$$^b$ | Toluene | C$_6$H$_{13}$C(OH)(CH$_3$)H | −1.07° (C, 13.5, B$^a$) | 10.7 |
| (−)TMCHD . LiAlH$_4$ | C$_6$H$_{13}$COCH$_3$$^c$ | Toluene | C$_6$H$_{13}$C(OH)(CH$_3$)H | −1.17° (C, 13.6, B$^a$) | 11.7 |

TABLE I-continued

| Chelate | Substrate | Solvent | Product | $[\alpha]_{589}^{25}$ | Optical Purity, % |
|---|---|---|---|---|---|
| (−)TMCHD . LiAlH$_4$ | C$_6$H$_5$COC$_4$H$_9$ | Toluene | C$_6$H$_5$C(OH)(C$_4$H$_9$)H | +1.75° (C, 13.7, B$^a$) | 5.6 |
| (+)TMCHD . LiAlH$_4^d$ | C$_6$H$_{13}$COCH$_3^c$ | Toluene | C$_6$H$_{13}$C(OH)(CH$_3$)H | +1.06° (C, 14.4, B$^a$) | 10.6 |
| (−)−TMCHD . LiAlH$_4$ | α-Tetralone$^c$ | Toluene | α-Tetralole | −0.97$^e$ (C, 2.50, C$^b$) | 3.9 |
| (−)−TMCHD . LiAlH$_4$ | β-Tetralone | Toluene | β-Tetralole | −2.32 (C, 7.8, C$^f$) | 8.2 |
| (−)−TMCHD . LiAlH$_4$ | C$_6$H$_{13}$COCH$_3$ | Toluene$^g$ | C$_6$H$_{13}$C(OH)(CH$_3$)H | −0.40 (C, 13.3, B$^a$) | 4.0 |
| (−)−TMCHD . LiAlD$_4$ | C$_6$H$_5$COH$^b$ | Toluene | C$_6$H$_5$C(OH)(D)H | −0.16 (neat) | 10.3 |
| (−)−TMCHD . LiAlH$_4$ | C$_6$H$_5$COCOH$^j$ | Toluene | C$_6$H$_5$C(OH)(CH$_2$OH)H | +4.91 (C, 2.04, E$^h$) | 8.3 |
| (−)TMCHD . LiAlH$_4$ | HOCH$_2$CH$_2$COCH$_3^b$ | Toluene | HOCH$_2$CH$_2$C(OH)(CH$_3$)H | +3.34 (C, 4.03, E$^h$) | >19.4$^i$ |
| (−)TMCHD . LiAlH$_4$ | HO(CH$_2$)$_3$COCH$_3^b$ | Toluene | HO(CH$_2$)$_3$C(OH)(CH$_3$)H | +.257° (neat) | ? |

$^a$B = Benzene
$^b$Molar ratio of chelate to substrate = 1:2.
$^c$Molar ratio of chelate to substrate = 1:4.
$^d$The (+)−TMCHD had $[\alpha]_{589}^{25}$ + 51.4° (C, 5.35, 95% EtOH) or 97% optical purity.
$^e$Rotation taken at 17° C.
$^f$C = chloroform.
$^g$Reaction run at room temperature.
$^h$E = 95% ethanol.
$^i$Optical purity ~30% when corrected for impurities by VPC analysis.
$^j$Molar ratio of chelate to substrate = 3:2.

The experimental results summarized in the above Table were obtained without any attempt being made to optimize reaction conditions to obtain maximum stereospecificity.

EXAMPLE 4

To 1020 ml of H$_2$O was added 114 g (1 mole) of trans-DACH and 150 g of d-tartaric acid and the hot solution was allowed to cool to room temperature and then to 0° C. Crop 1 DACH tartrate separated and was recovered by filtration, wt. 62.2 g (23.6%). The mother liquor was concentrated by removing 537 ml of water under reduced pressure and Crop 2 DACH tartrate separated, wt. 11.35 g (Crop 1+2=27.8% yield).

To the mother liquor from Crop 2 was added 108 g more of d-tartaric acid along with 45 ml of water and to the hot solution was added 2 liters of 95% ethanol. The hot solution was cooled very slowly to room temperature and finally to 0° C. and was held at the latter temperature for 48 hours. The fine needle-like crystals of DACH bitartrate were recovered by filtration and dried under vacuum @ 50° C., wt. 191.2 g (0.46 mole), $[\alpha]_{589}^{23}$ +24.7° (C, 5.1, H$_2$O).

The DACH bitartrate was dissolved in aqueous NaOH solution and the liberated (+)DACH was steam distilled from the mixture into dilute HCl. Steam distillation was contained until no more (+)DACH•2HCl was obtained upon evaporation of a aliquot of the steam distillate. A total of 118.3 g of crude undried (+)DACH•2HCl was obtained which was recrystallized from water yielding 53 g of recrystallized product (Crop 1), $[\alpha]_{589}^{22}$+9.5° (C, 20.0, H$_2$O). This material was again fractionally crystallized from water and 18.8 g of product was obtained which displayed $[\alpha]_{589}^{25}$+11.0° (C, 20.2, H$_2$O). A further recrystallization gave material having $[\alpha]_{589}^{25}$+12.2° (C, 21.86, H$_2$O) starting with 18.7 g of (+)DACH•2HCl of $[\alpha]_{589}^{25}$+11.0 and 5 g of (+)DACH•2HCl of $[\alpha]_{589}^{25}$+10.6° and obtaining therefrom 11.4 g of the thrice recrystallized (+)DACH•2HCl. (+)DACH•2HCl having $[\alpha]_{589}^{25}$+12.2° corresponds to 78% optical purity. Thus, the results of Examples 1 and 2 demonstrate that the procedure of fractional crystallization of neat (+)DACH is more efficient and gives higher yields of more nearly optically pure (+)DACH than does that of the prior art proceeding via the acid tartrate of (+)DACH followed by fractional crystallization of optically impure (+)DACH•2HCl from water.

EXAMPLE 5

To a 300 ml stirred autoclave was charged 23.33 g (80 mmoles) of N-(2-bromoethyl)phthalimide. The autoclave was evacuated and a solution of 9.12 g (80 mmoles) of (−)DACH in 100 ml of absolute ethanol containing 1 g of $C_{14}H_{30}$ was admitted. The autoclave was heated with stirring to 100° C. for 2.5 hours and then to 130° C. for 3 hours whereupon, by VPC analysis of a sample of the reaction mixture, reaction was deemed complete. The reaction mixture was pressured from the clave and the latter was washed with 100 ml of absolute ethanol. The combined ethanol solution was evaporated to dryness under reduced pressure affording 30.5 g of crude product to which was added 150 ml of water and 150 ml of 12 N HCl and the mixture was refluxed for 24 hours.

The hydrolysis reaction mixture was cooled in an ice bath and the precipitated phthalic acid was removed by filtration, wt. 12.1 g. The filtrate was evaporated under reduced pressure on a rotary evaporator until no more volatiles could be removed. To the residue was added 86 ml of 90% aqueous formic acid and 20 g of $NaHCO_3$ slowly. The mixture was heated to 80° C. and then 38 ml of 40% aqueous formaldehyde was added dropwise. The reaction mixture was refluxed with stirring for 36 hours, 23 ml of 12 N HCl was added and it was again evaporated under reduced pressure. Water, 50 ml, was added followed by an additional evaporation under reduced pressure. The residue was made basic with excess 50% aqueous NaOH solution and the liberated organic product was recovered by extraction with four 50 ml portions of hexane. Evaporation of the hexane gave a four component crude product which on a solvent free basis was 10.1% A, 80.7% B, 4.2% C and 5.07% D by VPC analysis. Component B was identified as (−)-TMCHD.

The above experimental procedure was repeated using 9.12 g of (−)-DACH and 40.66 g of N-(2-bromoethyl)phthalimide followed by 115 ml of formic acid, 27 g of $NaHCO_3$ and 50 ml of formaldehyde for the Eschweiler-Clarke methylation step. The crude methylated product had a similar composition as the first run by VPC analysis.

The crude products from both runs were combined and distilled. Cut I, bp 68° C. @ 3.5 mm, wt. 11.9 g; Cut II bp 69° C. @ 3.4 mm, wt. 3.4 g and Cut III bp 70°–99° C. @ 3.4–1.4 mm, wt. 5.4 g were obtained. VPC analysis gave the following compositions: Cut I 0.5% A, 90.9% B, 4.5% C and 0.3% D; Cut II 0.6% A, 91.7% B, 6.4% C and 0.3% D; Cut III 0.5% A, 29.4% B, 7.5% C and 61.7% D.

To Cut III, wt. 5.4 g, was added 9.73 g of n-hexane and 2.20 g of NaI and the mixture was stirred. Periodic VPC analysis indicated that the amount of component D remaining in solution was decreasing. After 18 hours, the mixture was filtered and the solid residue, wt. 4.76 g, was added to excess aqueous NaOH solution and the mixture was extracted with three 25 ml portions of hexane. The combined extract was dried and the hexane was stripped under vacuum. A clear, colorless liquid remained, wt. 2.58 g which by VPC analysis was 99+% pure D. This material was shown to be (−)-trans-1,2-N,N,N′-trimethyl-N′-(β-dimethylaminoethyl)cyclohexanediamine ((−)-PM-1,2-CHD) by 100 MHz NMR spectroscopy and elemental analysis: Theory for $C_{13}H_{29}N_3$; C, 68.67%; H, 12.85%; N, 18.48%. Found: C, 69.32%; H, 13.00%; N, 17.36%. The compound displayed $[\alpha]_{546}^{25} -13.95°$, $[\alpha]_{365}^{25} -29.30°$ (C, 0.2473 g in 5 ml benzene) using a Perkin Elmer model 141 polarimeter with a 10 cm microtube.

To 20 ml of toluene was added 1.93 g of (−)-PM-1,2-CHD and 0.45 g of $LiAlH_4$, the mixture was stirred overnight at room temperature and was then filtered. Evaporation of a portion of the filtrate gave a white solid which was (−)-PM-1,2-CHD•$LiAlH_4$, wt. 0.32 g. The remainder of the filtrate, estimated to contain about 6 mmoles of (−)-PM-1,2-CHD, was cooled to −80° C. and 2.12 g (16.5 mmoles) of 2-octanone dissolved in enough toluene to make 20 ml was gradually added over an hour with stirring. The reaction mixture was maintained at −75° to −80° C. for 15 minutes and then allowed to slowly warm to 0° C. Ice was added and gas was evolved. Then 55 ml of 0.5 N HCl was added, the organic phase was separated, washed with 15 ml of $NaHCO_3$ solution and 15 ml of water. After drying over $Na_2SO_4$ the toluene was stripped from the product under reduced pressure. The resultant oil, free of 2-octanone by VPC analysis, displayed $[\alpha]_{546}^{25} -0.32°$ (C, 13.4, benzene) which corresponds to 2.7% optical purity for 2-octanol.

EXAMPLE 6

A 1.09 g (3 mmole) portion of phenyl triphenylsilyl ketone $[C_6H_5COSi(C_6H_5)_3]$ was dissolved in 20 ml of toluene and the solution was cooled to −75° C. To the cold, stirred solution was added 1.5 mmoles of (−)-TMCHD•$LiAlH_4$ as a solution in toluene with stirring dropwise. After addition of the (−)-TMCHD•$LiAlH_4$ solution was complete the reaction mixture was stirred at −80° to −75° C. for 30 minutes and then allowed to warm to 0° C. whereupon it was hydrolyzed with ice and 20 ml of 1 N acetic acid. The organic layer was separated, extracted twice with 20 ml portions of 1 N HCl, once with 20 ml of saturated $NaHCO_3$ solution, once with 20 ml of water and was then dried over $Na_2SO_4$. Evaporation of toluene under reduced pressure gave an oil which solidified when scratched with a spatula. The product, $C_6H_5CHOHSi(C_6H_5)_3$, wt. 1.1 g, displayed $[\alpha]_{589}^{22} -6.91°$ which corresponds to 14% optical purity: lit. $[\alpha]_{589}^{22} +49.5°$ "J. Org. Chem.", 36, 21 (1971).

What is claimed is:
1. An asymmetric synthesis process for preparing optically active compounds which comprises the step of reacting an:
(a) organolithium compound complexed to an optically active chelating agent selected from the group consisting of Chel*•M-$Z_m$ wherein Chel* has a formula selected from the group consisting of:

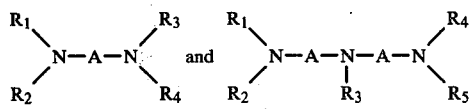

wherein $R_1$ is a $C_1$ to $C_{20}$ hydrocarbyl radical; $R_2$, $R_3$, $R_4$ and $R_5$ are the same or different alkyl or aryl radicals of 1 to 7 carbon atoms inclusive; A is selected from the group consisting of a nonreactive group containing 2 to 3 methylenic radicals having 1 to 6 monovalent substituents containing 1 to 10 carbon atoms, or a cycloaliphatic radical and their lower alkyl or naphthenic derivatives having ring structures containing 5 to 7 members wherein said radicals are attached to the nitrogen atoms at adjacent positions on the rings such that the chelating polytertiary amine does not have a center, plane or alternating axis of symmetry; x is an integer of 0 to 3 inclusive; M is lithium; Z is a reactive anion selected from the group consisting of $C_1$–$C_{30}$ alkyl, $C_6$–$C_{30}$ aryl, $C_2$–$C_{30}$ alkynyl, $AlH_4$ and $BH_4$; m is 1; with (b) a prochiral unsaturated carbonyl compound.

2. The process according to claim 1 wherein the prochiral unsaturated carbonyl compound is selected from the group consisting of aldehydes and ketones.

3. The process according to claim 1 or 2 wherein the Chel*•M-$Z_m$ material is (−)TMCHD•Li$C_6H_5$.

4. The process according to claim 1 or 2 wherein the Chel*•M-$Z_m$ material is (−)TMCHD•Li$C_4H_9$.

5. The process according to claim 1 or 2 wherein the Chel*•M-$Z_m$ material is (−)TMCHD•LiAl$H_4$.

6. The process according to claim 1 or 2 wherein the Chel*•M-$Z_m$ material is (−)TMCHD•LiB$H_4$.

* * * * *

UNITED STATES PATENT OFFICE
CERTIFICATE OF CORRECTION

Patent No. 4,165,330           Dated August 21, 1979

Inventor(s) Thomas A. Whitney and Arthur W. Langer, Jr.

It is certified that error appears in the above-identified patent and that said Letters Patent are hereby corrected as shown below:

IN THE CLAIMS:

Claim 1, Column 18, line 68, delete "x is an integer of 0 to"

Column 19, line 1, delete "3 inclusive."

Signed and Sealed this

Twelfth Day of January 1982

[SEAL]

Attest:

GERALD J. MOSSINGHOFF

Attesting Officer      Commissioner of Patents and Trademarks